United States Patent [19]

Mari

[11] Patent Number: 5,776,338
[45] Date of Patent: Jul. 7, 1998

[54] DISPOSABLE STERILE APPARATUS FOR BLOOD FILTRATION WITH A SYSTEM FOR OPTIMIZING THE RECOVERY OF BLOOD BETWEEN POUCHES

[75] Inventor: Giorgio Mari, Mirandola, Italy

[73] Assignee: Biofil s.r.l., Cavezzo, Italy

[21] Appl. No.: 755,284

[22] Filed: Nov. 22, 1996

Related U.S. Application Data

[63] Continuation of Ser. No. 292,464, Aug. 18, 1994, abandoned.

[51] Int. Cl.$^6$ .................................................. B01D 36/00
[52] U.S. Cl. ...................... 210/252; 210/254; 210/257.1; 210/418; 210/435; 210/436; 210/472
[58] Field of Search ........................ 210/767, 800, 210/252, 254, 257.1, 418, 435, 436, 472, 433.1, 136; 422/44, 101; 604/406, 409, 410.9

[56] References Cited

U.S. PATENT DOCUMENTS

| | | | |
|---|---|---|---|
| 4,115,277 | 9/1978 | Swank | 210/436 |
| 4,923,620 | 5/1990 | Pall | 210/767 |
| 4,997,577 | 3/1991 | Stewart | 210/767 |
| 5,128,048 | 7/1992 | Stewart et al. | 210/767 |
| 5,180,504 | 1/1993 | Johnson et al. | 210/767 |

FOREIGN PATENT DOCUMENTS

| | | |
|---|---|---|
| 9117809 | 11/1991 | WIPO. |
| 9405344 | 3/1994 | WIPO. |

*Primary Examiner*—John Kim
*Attorney, Agent, or Firm*—Rudnick & Wolfe

[57] ABSTRACT

A disposable sterile apparatus (1) for blood filtration with a system for the optimization of blood recovery in the passage from one pouch to the next, having a main tube (4, 8, 13, 18, 19) containing sterile air, one end of which is designed for the connection to a first container (pouch) (2) containing the liquid to be filtered and the other end of which is connected to a second empty container (pouch) (20). The foregoing tube (4, 8, 13, 18, 19) includes at least one filter (12) being arranged in the flow of the liquid. The apparatus (1) contains a tube (7) for the return of air from the second (20) to the first container (2) acting to equalize pressure of the liquid at the two extremities of the main tube (4, 8, 13, 18, 19) after the liquid has been filtered. The filter (12) features two interior semi-chambers with filtration material separating them. The first semi-chamber has an inlet port while the second semi-chamber has an outlet port and a venting port. Tubing (14) allows the venting port to communicate with the end of the main tube connected to the first container (2) so that the filter may be emptied.

6 Claims, 1 Drawing Sheet

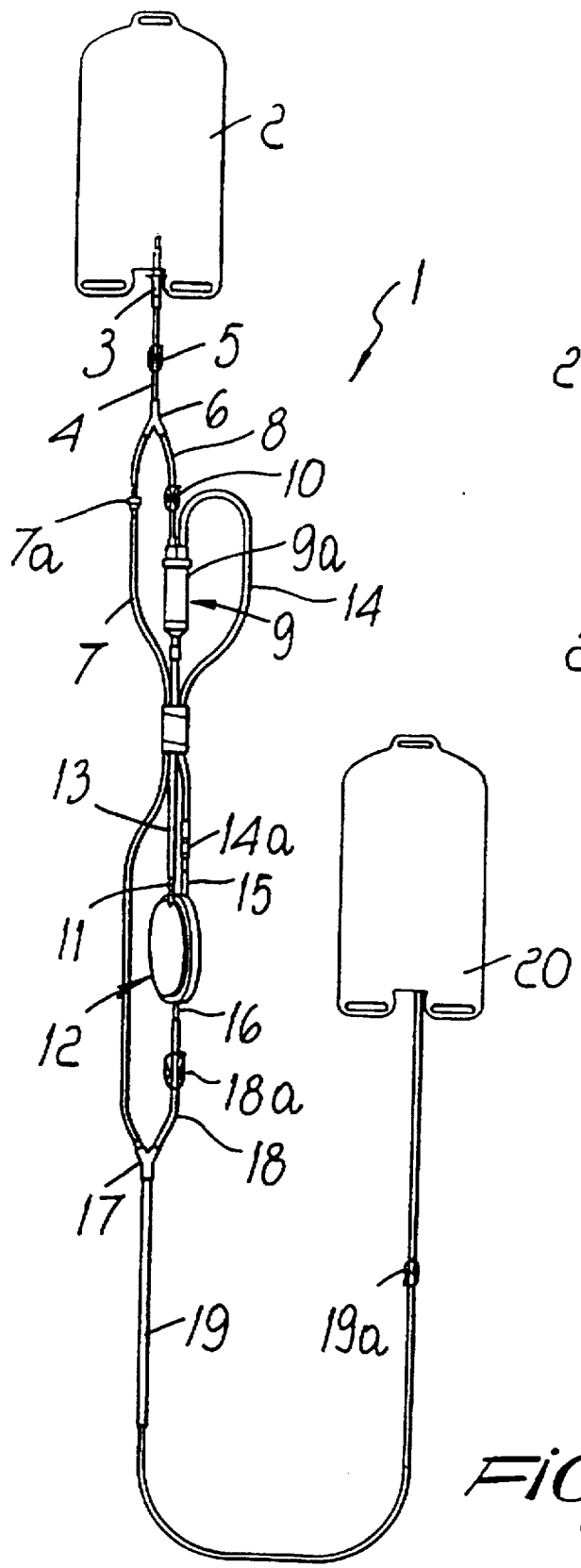
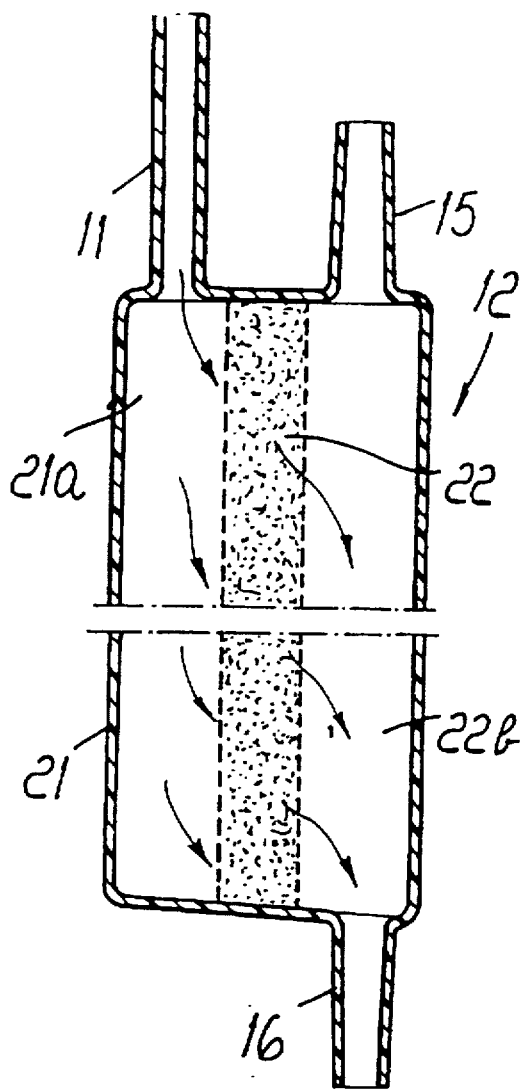
Fig. 1
Fig. 2

DISPOSABLE STERILE APPARATUS FOR BLOOD FILTRATION WITH A SYSTEM FOR OPTIMIZING THE RECOVERY OF BLOOD BETWEEN POUCHES

This application is a continuation of application Ser. No. 08/292,464, filed Aug. 18, 1994, now abandoned.

BACKGROUND

The present invention concerns a disposable sterile apparatus for the filtration of blood having a system for optimizing the recovery of blood in the passage from one container (pouch) to another.

The use of pre-assembled lines, designated tube sets, for single use to assure the sterility of the assembly for the filtration of blood contained in one pouch to a second empty pouch is now typical in the medical equipment sector. These sets are essentially composed of a tube in plastic equipped at the ends with quick couplings for a spike and a pouch that is empty of both liquid and air. At the center of the section of tube there is a filter designed to filter out any leukocytes contained in conserved blood and platelet concentrates, extraneous particles, etc. During use, the set is connected to a blood container, which is normally a pouch having the same dimensions and characteristics as the empty pouch, the container being suspended from a stand and, due to the effects of gravity, the medicament or the blood drips into the empty pouch. At the end of the process, i.e. when the upper container is empty, the final volume of liquid or blood present in the tube set tends to remain in the tube because of the negative pressure progressively created inside the assembly; because of this phenomenon a final quantity of blood or medical liquid is effectively lost during the filtration process.

Even if this negative pressure is relieved, because of the characteristic microporosity of the median filter element, and particularly, because after the filtration of blood the filter element tends to clog progressively thus reducing its degree of porosity in such a way that free air is no longer able to enter the filter medium, complete emptying of the pouch is prevented.

In practical terms, the so-called "bubble point" of the filter, this being the pressure value that the air must reach in order to pass through the capillaries of the filtration element soaked in blood, is not effectively reached. Therefore, the filter may not remain saturated.

To solve this problem, the Applicant has already developed a perfected filter, illustrated in FIG. 2, that comprises a filter body, having an inlet and an outlet, the filter being divided into at least two semi-chambers by an internal partition of filter material and one of these two chambers, the semi-chamber serving for evacuation being equipped with its own air inlet line in communication with the area external to the filter body.

Not withstanding the above, if outside air is utilized to allow the filter to be completely evacuated, an inlet filter is required for purification purposes. Moreover, the air cleaned by the inlet filter will inevitably be less pure than the sterile air.

The purpose of the present invention is to eliminate the problems mentioned above by developing a disposable sterile apparatus for the filtration of blood with a system for optimization of the recovery of filtered blood, which serves to recover the blood remaining in the filter in an optimized manner with respect to known apparatuses and to do this in a completely sterile ambient.

Within the framework of the foregoing purpose, one object of the present invention is to create an apparatus of simple design and high reliability that can be manufactured relatively easily and at competitive costs.

A second and equally important object is to create an apparatus with the use of fewer elements than known devices.

SUMMARY OF THE INVENTION

The above object, in conjunction with the forgoing purposes and other objects that will be outlined more clearly in the following pages, are achieved by means of a disposable apparatus for blood filtration with a system for the optimization of blood recovery, comprising a main tube containing sterile air, designed to be connected at one end to a first container containing the liquid to be filtered and the other end to an empty container, with said tube comprising at least one filter, characterized in that the filter has a line for the return of air from the |self-same| second container to the first container with the purpose of equalizing pressure of the liquid at the two ends of the tube (comprising at least one filter element) after the liquid has been filtered.

The characteristics and advantages of the invention will be clarified by the description of a preferred embodiment chosen for the purposes of illustration and shown in the drawings. dr

BRIEF DESCRIPTION OF THE DRAWINGS

FIG. 1 is a front elevation of an apparatus according to the present invention.

FIG. 2 is a cross section of a possible design of a filter utilized in the apparatus shown in FIG. 1.

DETAILED DESCRIPTION

With reference to the above-mentioned figures, 1 indicates an apparatus according to the present invention. 2 indicates a first container (pouch) containing the blood to be filtered. Container 2 is connected to the apparatus 1 by means of a spike 3 designed for insertion into an outlet of the container 2.

The spike 3 is connected to an initial section 4 of a main tube. On the initial section 4 of the main tube there is a tube clamp 5 for starting the filtration. The first initial section 4 of the main tube is connected to a three-way union 6, which connects the first initial section 4 of the main tube to an air return tube 7 and a second initial section 8 of the main tube. The air return tube 7 includes a check valve 7a that allows the passage of air only toward the first container 2.

A second initial section 8 of the main tube is connected to a drip chamber 9a of an initial aggregate filter 9. On the second initial section 8 of the main tube there is a safety tube clamp 10. The outlet from filter 9 is connected to a front connector 11 of a second selective filter 12 by means of an intermediate section 13 of the main tube. One end of an filter vent tube 14 for emptying the second filter 12 is connected to the top of the drip chamber 9a beside the second initial section 8 of the main tube. The other end of the tube 14 is connected to a rear connector 15 of the filter 12. Inside the filter vent tube 14 there is a break-off element 14a that permits the passage of liquid through tube 14 only when said element 14a has been fractured by the user.

An outlet of the second filter 12 comprises an outlet connector 16 located at the bottom of the second filter 12 on the side of connector 15. Moreover, outlet 16 of the second filter 12 is connected to a second three-way union 17 by means of a final section 18 of the main tube. On the first final section 18 of the main tube there is an air return tube clamp 18a. Moreover, the other end of the air return tube 7 is also connected to the three-way union 17.

Finally, an empty second container (pouch) 20 is connected to the outlet of union 17 by means of a second final section 19 of the main tube. The second final section 19 of the main tube includes a second safety tube clamp 19a.

It is emphasized that all the tubes in the apparatus disclosed in the invention will initially contain only sterile air and that the device is a "closed circuit system", that is, at no point during the process does external air enter the apparatus 1.

FIG. 2 shows a possible design of the selective filter 12 which is the subject of patent application M092UO0OO18. The filter 12 is essentially composed of a body 21 on which the front inlet connector 11 of the liquid to be filtered is located and also the rear connector 16 for emptying of the liquid to be filtered.

The filter body 21 is divided into at least two semi-chambers 21a and 21b which are, respectively, for the inlet of liquid to be filtered and the evacuation of the liquid after filtration, and a filter median partition 22. The front connector 15 serves to allow air to enter the evacuation semi-chamber 21b thus making it possible for the semi-chamber to empty completely.

Operation of the apparatus 1 in accordance with the claims of the present invention is as follows: spike 3 is inserted into the first container 2 containing the liquid to be filtered. The filtration start tube clamp 5 is opened and the liquid to be filtered enters the first 4 and second 8 section of the main tube. The inlet of liquid into the air return tube 7 is prevented by the check valve 7a. The liquid continues to flow toward the first filter 9, dripping slowly into the drip chamber 9a. The inlet of liquid into tube 14 for emptying of the second filter 12 is prevented by the connection of said tube 14 to the top of the drip chamber 9a. If the drip chamber 9a should fill with liquid the inlet to tube 14 is equally prevented by the break-off element 14a.

After passing through the intermediate section 13 of the main tube the liquid enters the second selective filter 12 by way of the front inlet connector 11. The liquid passes through the filter partition 22 and filtered liquid exits from filter 12 through the rear outlet connector 16 thus filling the empty container 20 by way of the first 18 and the second 19 final section of the main tube.

When the first container 2 is emptied, sections 4, 8, 13, 18 and 19 of the main tube will remain full of liquid to be filtered because of the reduced pressure. Also filter 12 will remain full of liquid to be filtered.

Once the first container 2 is empty, the second container 20 will contain the liquid from the first container 2 except for that liquid which has remained inside filter 12 and in the main tube 4, 8, 13, 18, 19 and the sterile air that was initially held in the main tube 4, 8, 13, 18, 19 and in the two filters 9, 12, which has been forced into second filtered liquid container 20.

At this point the air return tube clamp 18a must be closed and the second container 20 must be turned upside down and pressed thereby forcing the sterile air which it contains to flow through the air return tube 7, the check valve 7a and the first section 4 of the main tube so that it enters the first container 2.

Once the air from the second container 20 and the blood contained in the first initial section 4 of the main tube has passed to the first container 2 the air return tube clamp 18a must be opened. The pressure of the air surrounding the liquid contained in the tube and in the filters (9, 12) is now equalized and, due to the force of gravity, the liquid empties from the main tube (and container 2—the liquid previously contained in section 4), the first filter 9 and the first semi-chamber 21a of filter 12, descending toward the second container 20.

At this point the break-off element 14a is fractured thereby permitting air to pass through tube 14. The air remaining in the first container 2 is sufficient to empty the evacuation semi-chamber 21b of filter 12.

Since the air is free to pass through both inlet tubes 13 and 14 of filter 12, both the semi-chambers 21a and 21b of filter 12 are emptied, thereby further improving the recovery of filtered liquid.

The passage of air from one container to the other and the successive emptying of the tubes and the filters can, if necessary, be repeated several times.

It is also possible to compress the first container 2 to force the liquid transfer to the second container 20, even though this action is not strictly necessary since the effect of gravity is sufficient to recover liquid. Compressing the first container 2 is not recommended however, particularly when filtering blood, because the compression can give rise to modification of the corpuscular part of the blood. While the invention has been described by reference to one preferred embodiment chosen for the purposes of illustration, it should be understood that numerous changes could be made to details of the design without departing from the spirit and scope of the invention.

In practice, the materials used and the shapes and dimensions of the apparatuses can be varied limitlessly as required.

What is claimed is:

1. A disposable sterile apparatus for blood filtration having a system for optimizing the recovery of blood comprising:

a) a main tube, one end of the main tube being connectable to a first container for containing a liquid to be filtered and the other end being connectable to a second container for receiving filtered liquid;

b) at least one filter disposed along the main tube, the filter defining an interior chamber, filtration material partitioning the interior chamber into two semi-chambers, the first semi-chamber having an inlet port for the inlet of liquid to be filtered and the second semi-chamber having an outlet port for the outlet of filtered liquid, the second semi-chamber further having a connector communicating with the one end of the main tube by means of a filter vent tube;

c) an air return tube for facilitating the return of air from the second container to the first container thereby equalizing the pressure in the first and second containers, one end of the air return tube being connected to the main tube at a first connection point interposed between the one end of the main tube and the inlet port of the at least one filter, the other end of the air return tube being connected to the main tube at a second connection point interposed between the outlet port of the at least one filter and the other end of the main tube; and d) means for selectively preventing the passage of liquid from the second chamber of the at least one filter into the filter vent tube.

2. The apparatus of claim 1, further comprising a check valve disposed on the air return tube for preventing the passage of fluid from the first container to the second container and for permitting the flow of air from the second container to the first container.

3. The apparatus of claim 1, further comprising valve means for selectively stopping the flow of liquid from the main tube to the second container and preventing the flow of air into the main tube when air is flowing from the second container to the first container, the valve means being interposed between the outlet port of the at least one filter and the second connection point.

4. A disposable sterile apparatus for blood filtration having a system for optimizing the recovery of blood comprising:

a) a main tube, one end of the main tube being connectable to a first container for containing a liquid to be filtered and the other end being connectable to a second container for receiving filtered liquid;

b) at least one filter disposed along the main tube, the filter defining an interior chamber, filtration material partitioning the interior chamber into two semi-chambers, the first semi-chamber having an inlet port for the inlet of liquid to be filtered and the second semi-chamber having an outlet port for the outlet of filtered liquid, the second semi-chamber further having a connector communicating with the one end of the main tube by means of a filter vent tube;

c) an air return tube for facilitating the return of air from the second container to the first container thereby equalizing the pressure in the first and second containers, one end of the air return tube being connected to the main tube at a first connection point interposed between the one end of the main tube and the inlet port of the at least one filter, the other end of the air return tube being connected to the main tube at a second connection point interposed between the outlet port of the at least one filter and the other end of the main tube; and d) a drip filter interposed between the first connection point and the inlet port of the at least one filter, said drip filter including a chamber to the upper wall of which there is connected the one end of the filter vent tube, the other end of the filter vent tube being connected to the connector of the second semi-chamber of the at least one filter.

5. The apparatus of claim 4, further comprising a check valve disposed on the air return tube for preventing the passage of fluid from the first container to the second container and for permitting the flow of air from the second container to the first container.

6. The apparatus of claim 4, further comprising valve means for selectively stopping the flow of liquid from the main tube to the second container and preventing the flow of air into the main tube when air is flowing from the second container to the first container, the valve means being interposed between the outlet port of the at least one filter and the second connection point.

* * * * *